United States Patent [19]

Woog et al.

[11] 4,078,558

[45] Mar. 14, 1978

[54] ORAL HYGIENE APPARATUS

[75] Inventors: Philippe-Guy E. Woog; Michel Antoine C. Moret, both of Geneva, Switzerland

[73] Assignee: Les Produits Associes LPA SA, Switzerland

[21] Appl. No.: 704,330

[22] Filed: Jul. 12, 1976

[30] Foreign Application Priority Data

Dec. 9, 1975 Switzerland ............. 15968/75

[51] Int. Cl.² .............................................. A61H 9/00
[52] U.S. Cl. ...................................... 128/66; 134/93; 134/184; 128/230; 366/114
[58] Field of Search ................. 128/65, 66, 62.1, 230; 259/18, DIG. 44; 134/93, 100, 184

[56] References Cited

U.S. PATENT DOCUMENTS

| 3,044,465 | 7/1962 | Anderson et al. | 128/230 |
| 3,495,587 | 2/1970 | Freedman | 128/66 |
| 3,669,101 | 6/1972 | Kleiner | 128/66 |
| 3,820,532 | 6/1974 | Eberhardt et al. | 128/66 |

Primary Examiner—Lawrence W. Trapp

Attorney, Agent, or Firm—Kane, Dalsimer, Kane, Sullivan and Kurucz

[57] ABSTRACT

An apparatus for personal hygiene, in particular for oral hygiene which includes a reservoir removably fitted on a casing for containing a liquid supply, and, furthermore, structure is provided for receiving a dispenser of a hygienic, cosmetic or therapeutic product, in particular a dentifrice solution, for addition to the liquid in the reservoir. For facilitating bucco-dental hygiene, the apparatus also includes a hydraulic pump within the casing connected by a flexible tubing to a handpiece having any particular type of spray head. The reservoir is adapted to supply liquid to the pump and, at the same time, is designed to receive the dentifrice solution from the dispenser. The dispenser structure can be independently formed and mounted on the apparatus casing or can be incorporated into the reservoir structure. The apparatus is also designed to serve as a cleaning device for dentures, and in this connection, the dispenser would contain a cleaning fluid for dispensing into the reservoir. An appropriate agitator can be employed as part of the structure when it is used for cleaning dentures.

44 Claims, 27 Drawing Figures

FIG. 26

ORAL HYGIENE APPARATUS

BACKGROUND OF THE INVENTION

There are commercially available a liquid-treatment apparatus for body care, and particularly for bucco-dental hygiene. Such apparatus generally includes a casing enclosing a hydraulic pump connected by a flexible tubing to a handpiece having a spray head, and a reservoir removable fitted on the casing for supplying liquid to the pump. This type of apparatus providing a pulsed jet of liquid is efficient both for cleaning the teeth and flushing out particles stuck between the teeth as well as for massaging the gums and stimulating blood circulation therein. In some "combined" apparatus, the spray nozzle can be replaced by a toothbrush which is oscillated by a hydraulic motor housed in the handpiece. In both of these types of devices, the reservoir is removably connected to the pump inlet by a suitable valve to supply water to the pump independently of the water supply. In certain types of apparatus the reservoir is formed by a removable cover which is reversible to receive the water and to connect with the pump to provide the water supply. Other alternative forms include a reservoir with a gripping handle and a pivoted lid with the reservoir resting on a lateral projection on the casing and being of shape and dimensions to complete the geometrical configuration of the casing. The content of such a reservoir may be from ½ liter to 1 liter of water, which is sufficient for the buccal treatment in question, and makes handling easy, even for children.

It has also been proposed to use dentifrice rinses for prophylactic purposes and prevention of dental plaque this becoming ever increasingly necessary in view of the fact that 98% of the population suffers from dental decay and more than 90% of persons in the over 40 age group suffer from periodontal disease despite all of the dental hygiene measures taken to date.

Long research and practical experience have shown that chlorhexidine solutions are the most efficient products for this purpose. Tests have shown that concentrations slightly less than 0.2% of chlorhexidine gluconate can substantially delay the formation of dental plaques, and in particular a concentration of 0.025 to 0.05% is sufficient to obtain an excellent hygiene. The distribution of chlorhexidine to the different parts of the teeth and the consequent prevention of the formation of dental plaque may also be improved by use of an oral irrigation device. Further, it has been observed that the coloring effect which may occur because of the presence of chlorhexidine is considerably reduced if large volumes of low-concentration liquid are also used. Tests have shown that 700 ml of 0.1% chlorhexidine solution does not produce any more coloration than a neutral liquid whereas 20 ml of a 0.2% solution produces an apparent coloration.

To achieve perfect mouth hygiene it would thus be possible to use the two aforesaid means, in turn, i.e., on the one hand, cleaning the teeth and massaging the gums by an apparatus of the described type, and on the other hand rinsing with a dentifrice solution. However, to achieve such complete hygiene would require several time-consuming operations. People, usually in a hurry, in general sacrifice relatively little time for body care and in particular buccal hygiene, to the detriment of their health and prophylaxis. In fact, experience has demonstrated that it is unrealistic to expect people to regularly carry out such successive operations.

SUMMARY OF THE INVENTION

With the above background in mind, it is among the primary objectives of the present invention to provide as a totally new concept apparatus of the type described that is capable of efficient bucco-dental treatment and prophylaxis without increasing the time of treatment while simplifying overall treatment.

To this end, an apparatus of the aforementioned type is characterized in that it incorporated means for receiving a dispenser of a hygienic, cosmetic or therapeutic product, in particular a dentifrice solution, for addition to the liquid in the reservoir. In one embodiment, the receiving means is formed by an accomodating recess in the upper part of the casing. Other embodiments include receiving means associated with the reservoir or on a hinged lid therefore in which case either the dispenser alone or together with the lid can be removed and replaced as desired. Alternatively, when the reservoir is formed by inverting the cover of the casing the recess for the dispenser can be formed on the cover structure or the dispenser can be mounted on a separate lid positioned on the cover when it is inverted.

It is also contemplated that solid tablets or pills can be employed in lieu of a solution. In such cases the dispenser will be appropriately positioned on the casing or lid of the reservoir to assure introduction of the additives into the reservoir. A further embodiment incorporates a safety means on the dispensing structure to assure the dispensing of a predetermined amount of solution into the reservoir thereby making it difficult for a person or in particular a child to dispense an excess amount of solution.

In a further embodiment dentures may be cleaned. The dispenser structure can be conveniently positioned for introduction of a cleaning solution to the reservoir. If desired, suitable agitation means can be provided on the structure to facilitate cleaning after the appropriate solution has been introduced into the reservoir.

With the above objectives among others in mind, reference is had to the attached drawings.

BRIEF DESCRIPTION OF THE DRAWINGS

In The Drawings:

FIG. 14a is a top plan view thereof showing the lid detached from the reservoir;

DESCRIPTION OF THE PREFERRED EMBODIMENT

In the embodiment of FIGS. 1–3b, the apparatus consists of a casing 1 which contains a hydraulic pump coupled with an electric motor, and of which only external control buttons 2 and 3 are shown. A handpiece 4 is held vertically in a recess 11 of casing 1, and is connected by a flexible tube 5 to the hydraulic pump. On the handpiece 4 is fitted a spray head 6, and several spare interchangeable spray heads 6a, 6b and 6c are stored upstanding in suitable receptacles 7 in casing 1.

Casing 1 has a lateral projecting part defining a shelf 1a adapted to receive a removable reservoir 8. On one of its lateral faces, this reservoir 8 has an overflow slot 12 and on another face a handle 9 fixed to the upper part of the reservoir for facilitating gripping and carrying the reservoir. A lid 10 is connected by a hinge to the reservoir 8 and has, adjacent the handle 9, an upstanding projection 10a which enables the lid 10 to be opened by the thumb of the hand holding the handle 9. The reservoir 8 further has, in its lower part, a known type of valve which connects with the pump of the apparatus. The body 18 of reservoir 9 which bears against the casing 1 has a projecting profile which fits in a complementary recess in the casing to exactly position the reservoir 8 on casing 1. The shape of the reservoir 8 is such that, when fitted, three of its side faces are flush with and in extension of the corresponding faces of the casing, and the lid 10 in its rest position is in the same plane as the upper face of casing 1. The fitted reservoir 8 and casing 1 thus form a compact unit.

A hollow recess 13 is formed in the upper face of the casing adjacent the reservoir 8 for receiving a removable diffuser or dispenser 14 containing a hygienic product, in particular a dentifrice solution, which is advantageously and conveniently adapted to be added to the liquid contained in reservoir 8.

A projecting nozzle 15 of dispenser 14 has its opening 16 directed obliquely to deliver product into the reservoir 8, when the lid 10 is open. In the depicted embodiment, nozzle 15 bears against the upper face of casing 1 when the dispenser is placed in recess 13, and the dimensions of nozzle 15 are such that it does not obstruct the removal or replacement of reservoir 8, nor the opening or closing of lid 10 when the reservoir 8 is fitted on casing 1. As variation, this nozzle 15 could be replaced by a duct incorporated in the upper part of the casing.

Figure 1:
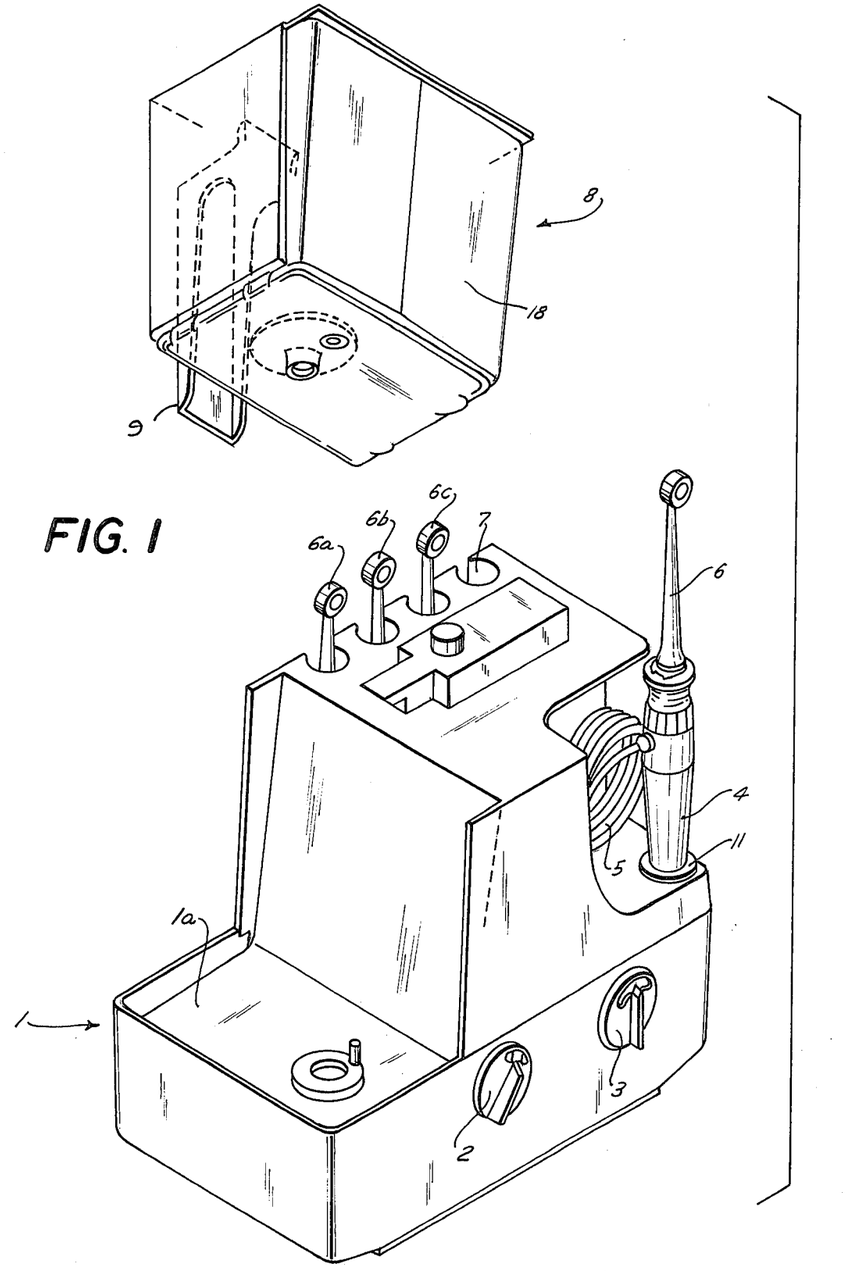
FIG. 1 is an exploded perspective view of a first embodiment of oral hygiene apparatus incorporating the teachings of this invention with the reservoir removed.
Figure 2:
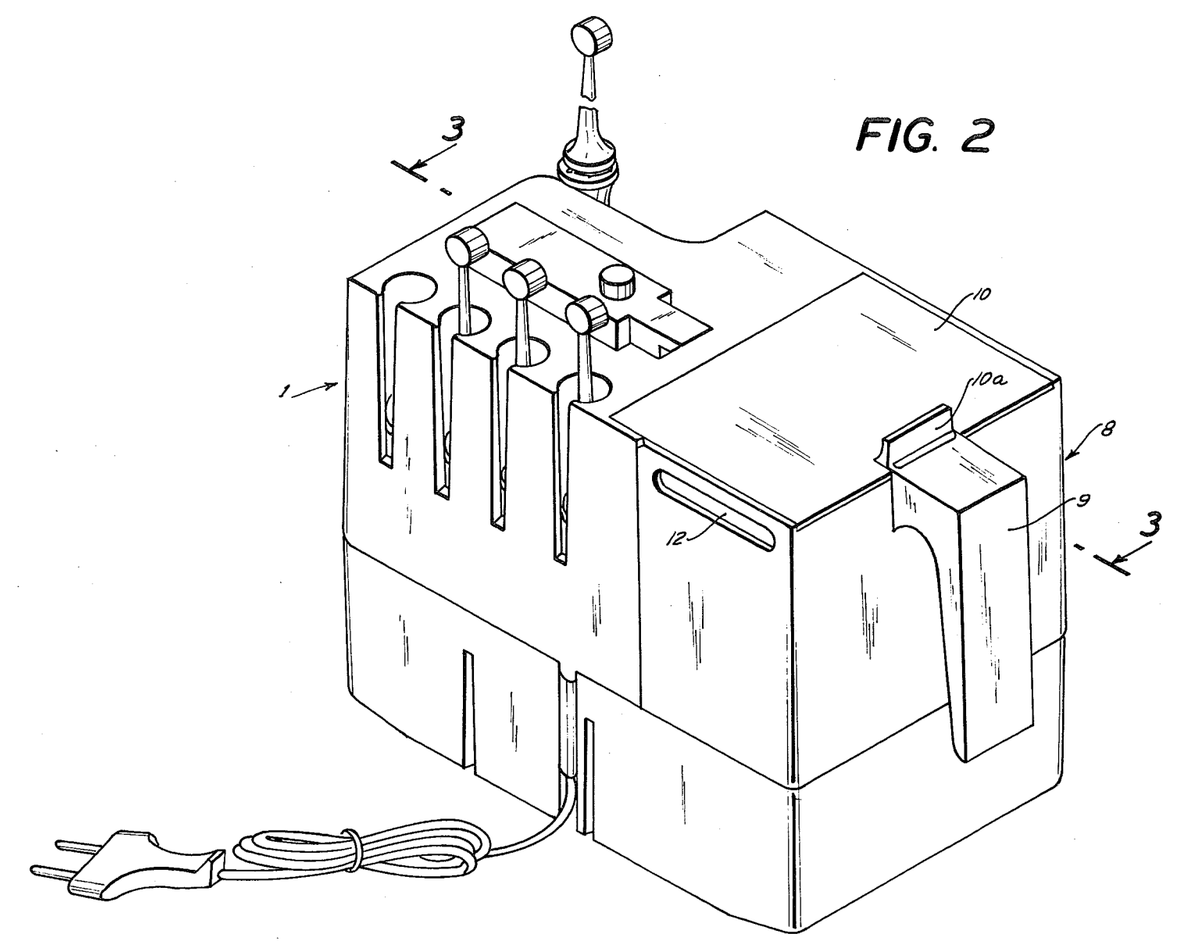
FIG. 2 is a perspective view thereof with the reservoir assembled.
Figure 3A:
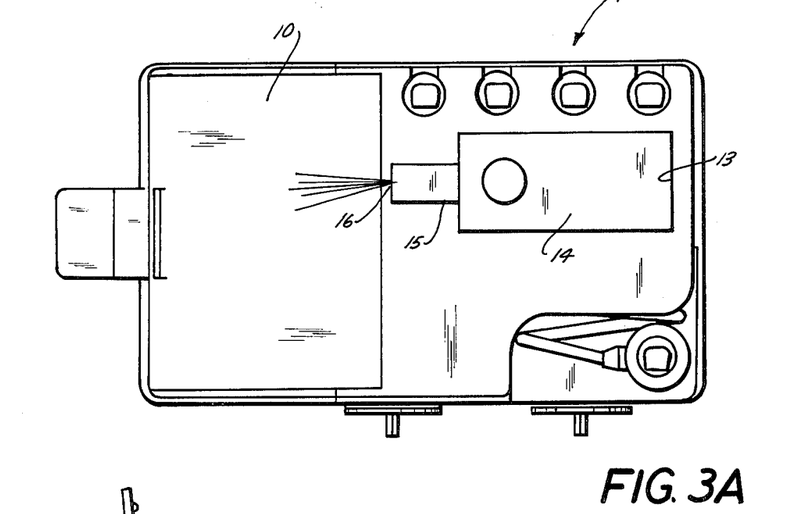
FIG. 3a is a top plan view thereof.
Figure 3B:
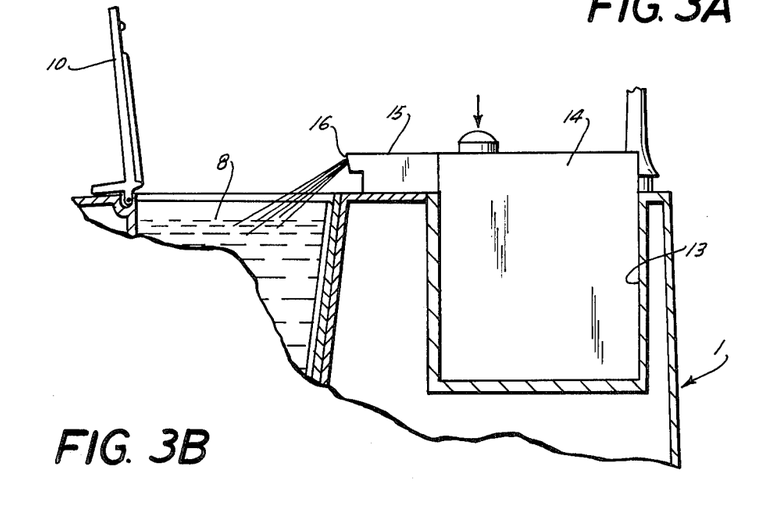
FIG. 3b is a fragmentary sectional side elevation view thereof taken along the lines 3—3 of FIG. 2 with the lid open and the spray head removed.
Figure 4:
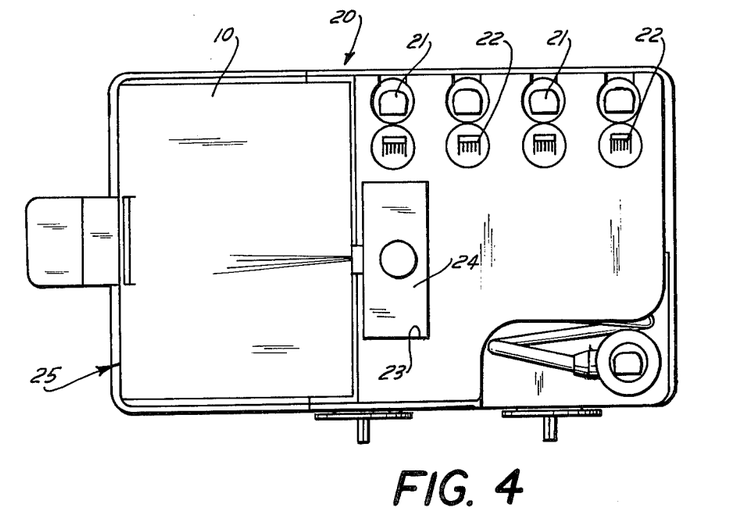
FIG. 4 is a top plan view of a second embodiment of apparatus of this invention.
Figure 5:
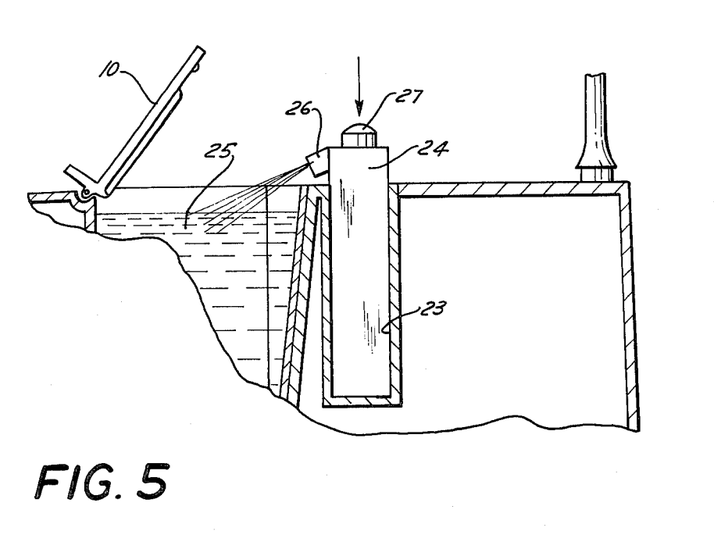
FIG. 5 is a fragmentary sectional elevation view thereof.

FIGS. 4 and 5 show a second embodiment of apparatus which may be used both for brushing the teeth and spraying a liquid. For this purpose, casing 20 has four spray nozzles 21 and four tooth brushes 22 stored in parallel rows. A recess 23 of rectangular section is arranged close to the fitted reservoir 25, perpendicular to the upper face of the casing, to receive a corresponding dispenser 24. An outlet nozzle 26 of dispenser 24 is directed obliquely, toward the interior of the reservoir 25.

The dispenser 24 is in the form of a cartridge or flask and may even be an aerosol dispenser provided at its upper end with a push button 27.

Figure 6:
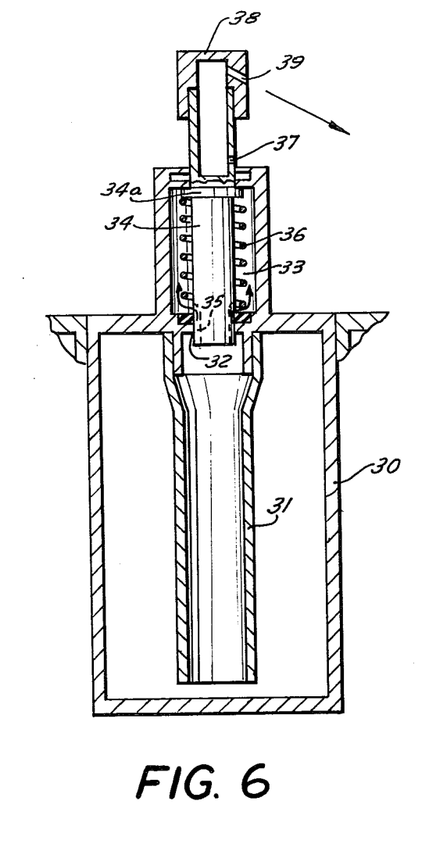
FIGS. 6 and 7 are cross sectional views of a first form of contemplated dispenser in the rest and discharge positions, respectively.
Figure 7:
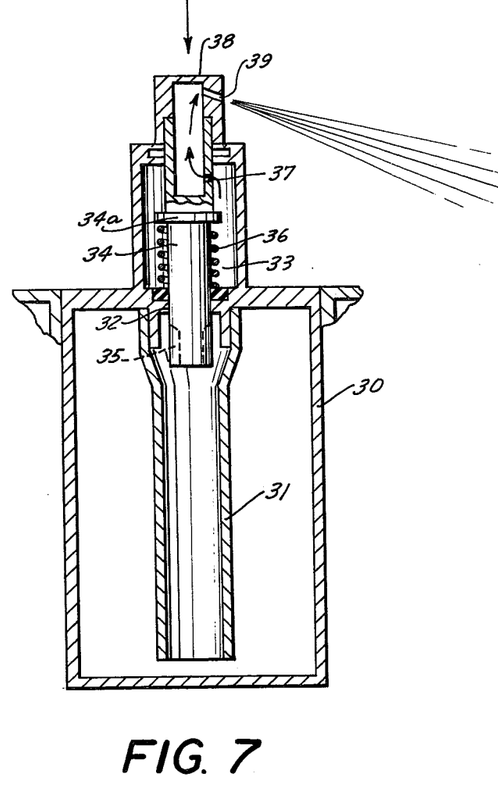

FIGS. 6 and 7 show a form of cartridge adapted for use with the apparatus of this invention in its rest and dispensing positions, respectively. The cartridge 30, enclosing a liquid under pressure or a liquefied gas with the active product, has a plunger tube 31 connected below an opening 32 which connects the interior of the cartridge with an upper chamber 33. A sliding rod 34 having a shoulder 34a passes through the upper wall of upper chamber 33, and its lower end has two longitudinal slots 35 which, in the rest position, pass through opening 32. A spring 36 holds rod 34 in the rest position, in which the product in the cartridge can, as indicated by the arrows in FIG. 6, pass through slots 35 into the upper chamber 33. The hollow upper end of rod 34 has in its lower position, above shoulder 34a, a transfer orifice 37 and is capped with a hollow button 38 having an outlet spray orifice 39.

By downwardly depressing the rod 34 by acting on button 38 against the action of spring 36, the rod 34 is made to penetrate in opening 32, and the non-perforated central part of rod 34 prevents the passage of liquid from inside the cartridge into the upper chamber 33. Simultaneously, the dose of product contained in the upper chamber 33 can pass through orifice 37 and is released via the spray orifice 39 as indicated by the arrow in FIG. 7.

Figure 8:
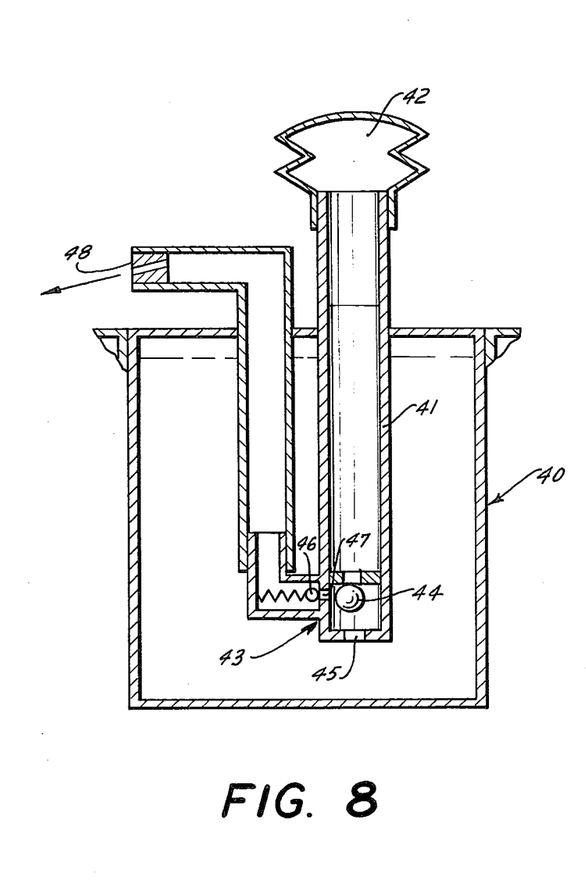
FIGS. 8 and 9 are cross sectional views of a second form of dispenser in a rest and a discharging position, respectively.
Figure 9:
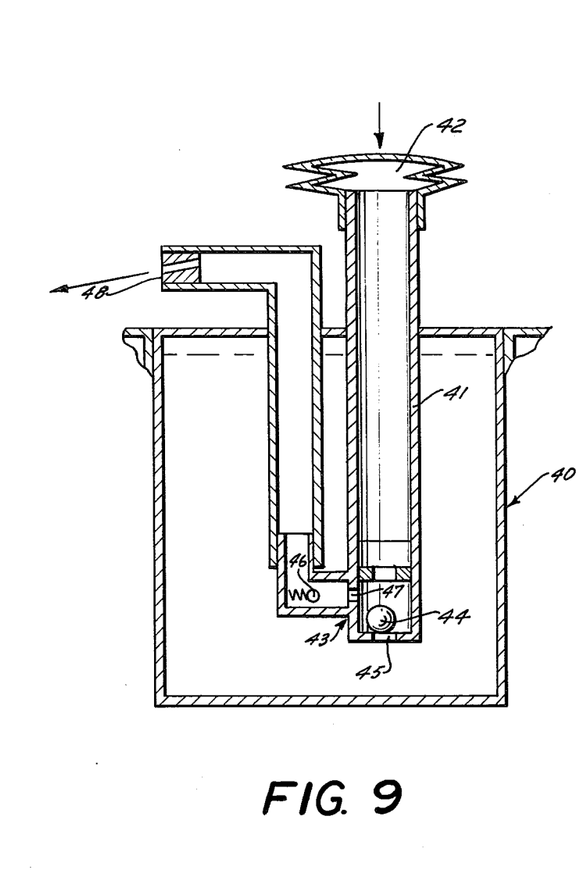

In the embodiment shown in the rest and spray positions in FIGS. 8 and 9 respectively, cartridge 40 is provided with a plunger tube 41 having an external, deformable chamber 42 forming a bellows-like push-button, and a ball valve 43. Pressure on chamber 42 pushes a ball 44 against an inlet opening 45 and disengages a spring-biased ball 46 from an outlet opening 47 communicating with a spray nozzle 48. Upon releasing chamber 42, the valve relaxes under the suction effect and a new dose of liquid fills the plunger tube 41 for the next dispensing action.

Figure 10:
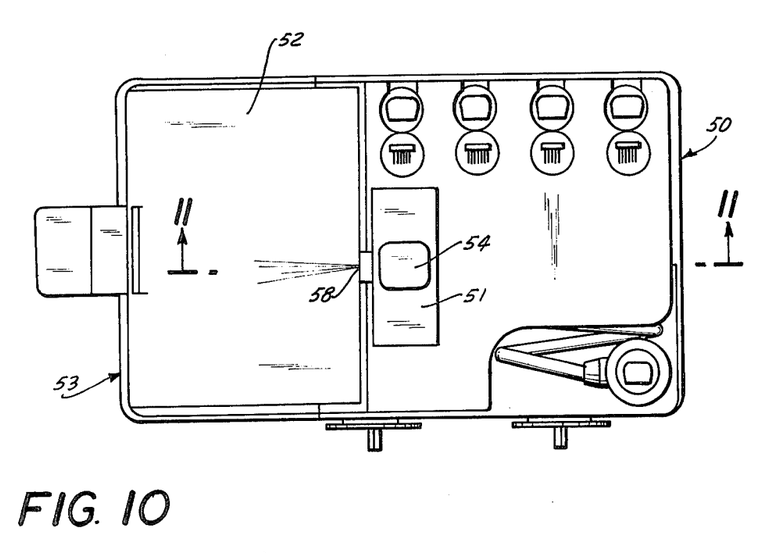
FIG. 10 is a top plan view of a third embodiment of apparatus of this invention.
Figure 11:
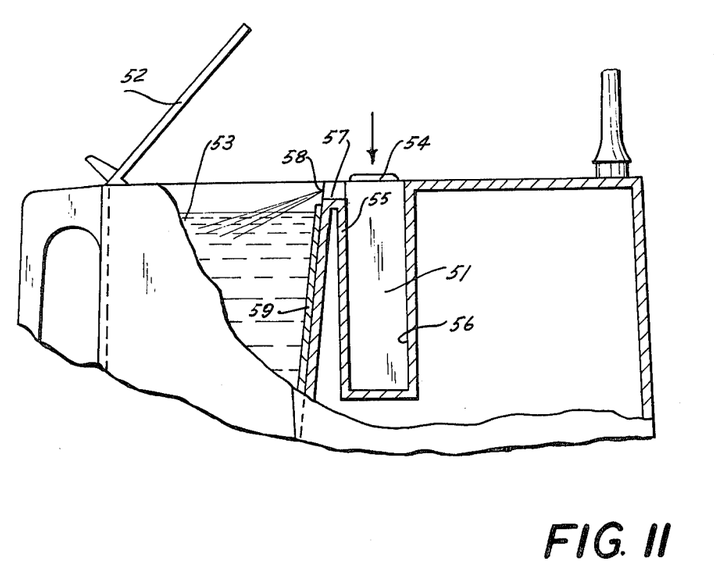
FIG. 11 is a fragmentary sectional elevation view thereof taken along the plane of lines 11—11 of FIG. 10.

FIGS. 10 and 11 show a further embodiment of the apparatus and dispenser. In this embodiment, dispenser 51 has a height such that its upper face is flush with the upper face of the associated casing 50 and the lid 52 of reservoir 53. Only push-button 54 protrudes slightly above this upper level, but it could alternatively be in the same plane. Dispenser 51 has an outlet beak or nozzle 58 whose orifice is situated below the level of closed lid 52. The wall 55 of the casing defining the dispenser receiving recess 56 has an upper notch or opening 57 receiving the nozzle 58 whose outlet orifice is directed into the reservoir. The adjacent wall 59 of reservoir 53 also has a corresponding notch or opening allowing the nozzle 58 to directly face into the reservoir. With this embodiment, it is possible to dispense the product into the reservoir without having to lift up the lid 52. Additionally, the unit formed by the casing, reservoir and distributor has a common flat upper face.

Figure 12:
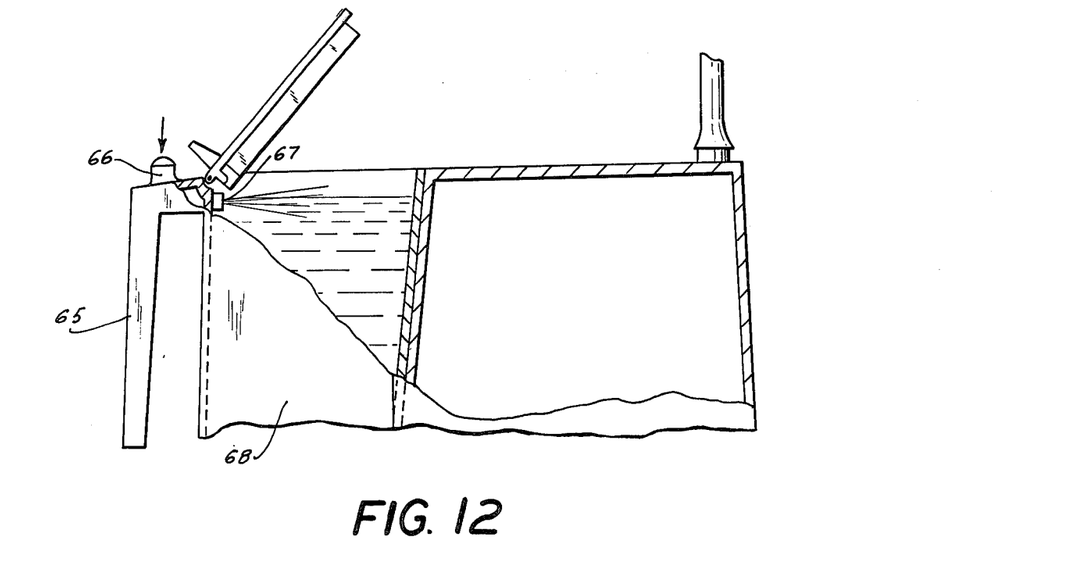
FIG. 12 is a fragmentary sectional elevation view of a fourth embodiment of the apparatus of this invention with the dispenser incorporated as part of the reservoir construction.
Figure 13:
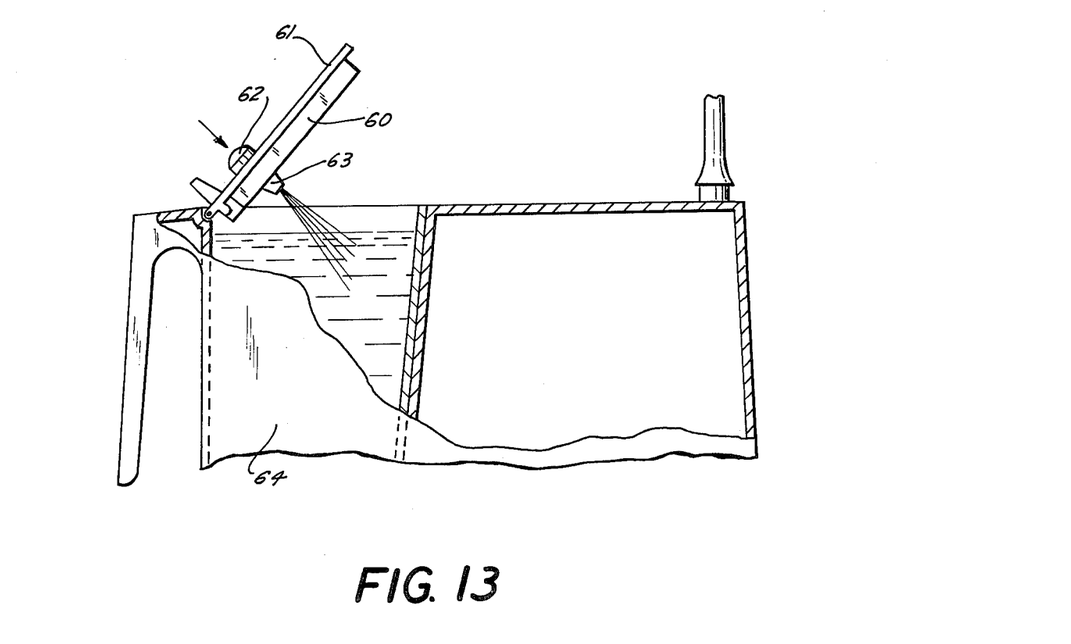
FIG. 13 is a fragmentary sectional elevation view of a fifth embodiment of the apparatus.

FIG. 13 shows an embodiment of the apparatus with a dispenser 60 removably secured on the inner face of lid 61. Dispenser 60 has a push-button 62 accessible through an appropriate opening of cover 61 and a spray nozzle 63 directed into the reservoir 64. As a variation, as shown in FIG. 12, the dispenser could be fitted in the reservoir handle 65 with a push-button 66 on the upper surface of the handle to dispense fluid through a nozzle 67 extending through the side wall of the reservoir 68. The dispenser can also be located in one of the walls of the reservoir and can be secured to the casing or to the reservoir by any known means, for example a resilient clip, interengaging hooks, and the like.

Figures 14, 15, 17:
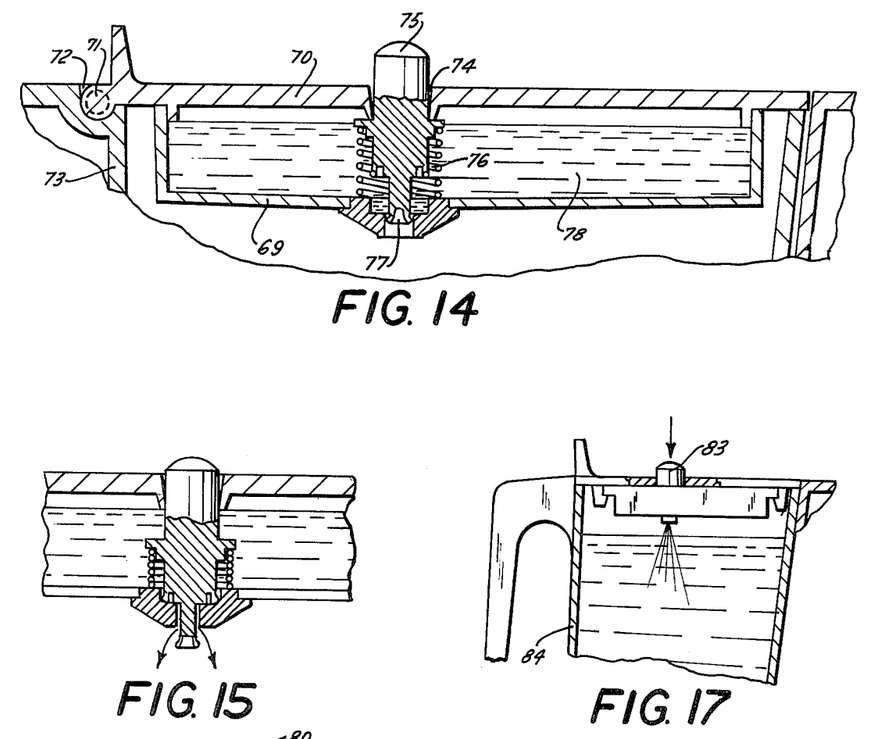
FIG. 14 is a fragmentary sectional elevation view of a sixth embodiment of the invention showing the dispenser in the closed position.
FIG. 15 is a fragmentary sectional elevation view thereof showing the dispenser in position for dispensing fluid.
FIGS. 16 and 17 are fragmentary sectional elevation views of a seventh embodiment of the invention showing a dispenser being introduced and interconnected with the underside of the lid of the reservoir, respectively.

The present invention also contemplates providing a lid and dispenser as a unit, as shown in FIGS. 14 and 14a which can be replaced by the user when the dispenser is empty. The dispenser 69 is integrally formed with lid 70 or may be permanently coupled therewith by conventional means. The lid contains a pair of opposing prongs 71 which can be snapped into opposing recesses 72 in reservoir 73. The snap-in feature is obtained by using a material with sufficient resilience for the lid and reservoir such as any one of many known and conventional plastic materials having such properties. The lid has a central recess 74 through which extends a push-button 75. Depression of the push-button 75 against the bias of spring 76 opens the valve 77 at the base of the dispenser and permits the solution 78 to enter the interior of reservoir 73 as shown by the arrows in FIG. 15. Release of button 17 permits spring 76 to return the button to the initial position of FIG. 14, once again closing the valve when the desired amount of solution has been dispensed.

Figure 16:
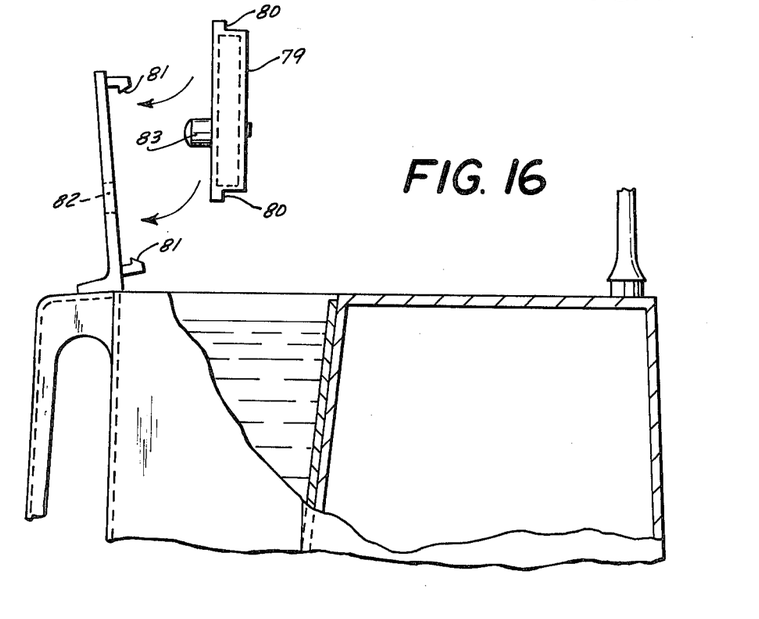

A further embodiment is depicted in FIGS. 16 and 17. The difference in structure resides in the nature of coupling of the dispenser to the lid. In place of the integral coupling of dispenser and lid of the previous embodiment where the combined structure is replaceable as a unit, the embodiment of FIGS. 16 and 17 employs a snap-in dispenser 79 which has a pair of opposing lips or flanges 80 which are adapted to snap into position in the recess formed by receiving hooks 81. The material for receiving hooks 81 is of sufficient resilience to permit the introduction of the dispenser 79 into the position to be held by the hooks. A recess 82 is provided in the lid for passage of push-button 83 therethrough to be operated in the same manner as in connection with the previous embodiment. Lid 82 is opened and dispenser 79 is snapped into position whereupon lid 82 can be closed and solution dispensed by depression of push-button 83. The fluid is directed into the reservoir 84 as depicted in FIG. 17.

Figure 18:
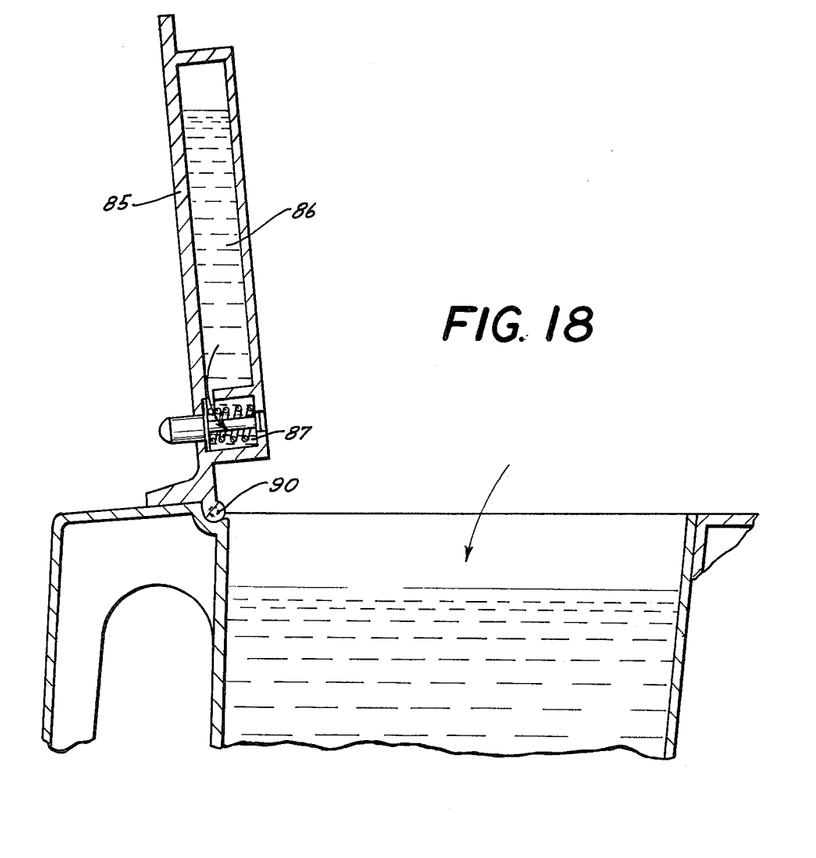
FIGS. 18 and 19 are fragmentary sectional elevation views of an eight embodiment of the invention showing the lid in the open position for introduction of solution to a dispensing position and the lid in the closed position and the fluid being dispensed therefrom, respectively.
Figure 19:
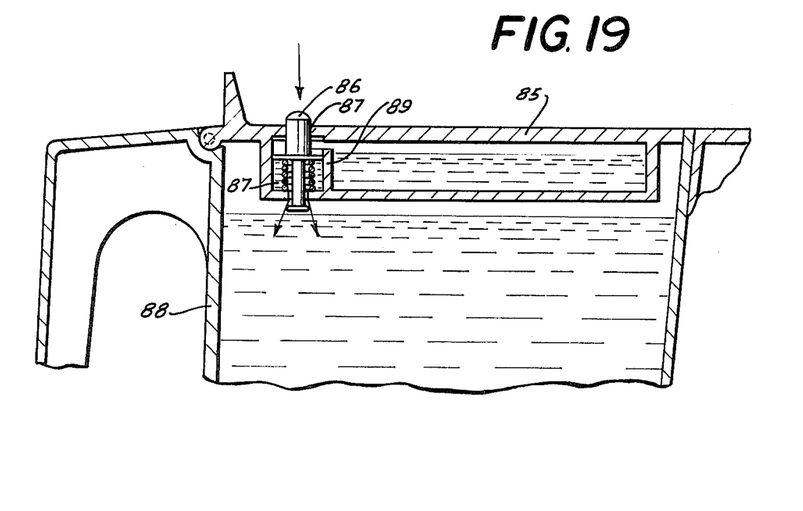

FIGS. 18 and 19 disclose a safety embodiment which makes it difficult for anybody, particularly a child, to press several times on the button thereby providing a solution with too high a concentration of additive in the reservoir. When the lid 85 is lifted, solution 86 will flow into the dispensing chamber 87 as shown by the arrow in FIG. 18. Thereafter when the lid 85 is closed and push-button 86 is depressed through opening 87 in the lid, fluid will be dispensed from chamber 87 through the open valve as indicated by the arrows in FIG. 19 into the reservoir 88. Further fluid is prevented from entering dispensing chamber 87 by the presence of wall 89 so that additional depressions of button 86 to reopen the valve will not permit any further fluid to be expelled since chamber 87 will have been emptied. To refill chamber 87 it is necessary to once again open lid 85 by pivoting about its hinge 90 whereupon liquid will once again fill chamber 87 in the manner depicted in FIG. 18. The lid can then be closed again and a further dose of liquid in chamber 87 can be dispensed in the same manner. A solution in the dispenser fills the release system only when the cover of the reservoir is lifted. This means that there is a necessary sequence of operations, first lifting the cover, second closing the cover, and third pressing on the button. This makes it very difficult for a child to inject in the reservoir more than the prescribed dose of product. Naturally there are other means for achieving the same objective such as the inclusion of a timer, the progressive release of a spring through a bellow system or the cocking of the release system by a mechanical means when the reservoir cover is opened.

Figure 20:
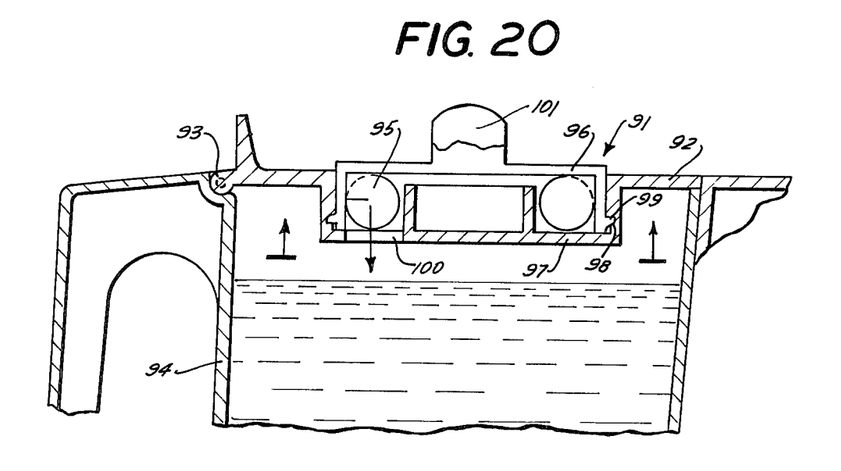
FIG. 20 is a fragmentary sectional elevation view of a ninth embodiment of the invention.
Figure 21:
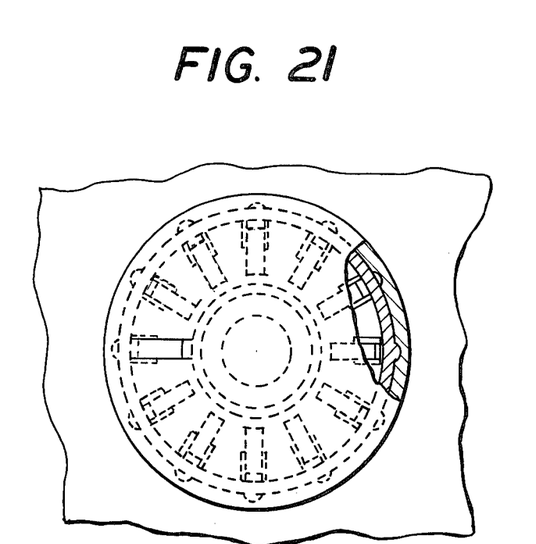
FIG. 21 is a fragmentary cross sectional view thereof taken along the plane of lines 21—21 of FIG. 20.

FIGS. 20 and 21 are directed to an embodiment for dispensing tablets or pills rather than a liquid into the reservoir for use. This type of system is desirable where chemicals are presented to the public in a solid form whether it is a tablet, effervescent or not, a pill, a powder, a jell, or the like. The dispenser 91 is mounted in the lid 92 attached by a hinge 93 to the reservoir 94. The tablets 95 are housed within a cylindrical casing 96 which is snapped into position within a receiving well 97 in the lid 92. Appropriate notches 98 are in the walls of the receiving well to receive the resiliently snapped-in tabs 99. The base of the receiving well 97 contains an opening 100 through which a tablet 95 may be dispensed when it is aligned with the opening into contact with the liquid in the reservoir 94. The central portion of the dispenser 91 is rotatable and contains an upwardly extending knob 101 so that the tablets can be rotated in sequence into alignment with opening 100 for dispensing purposes. An appropriate safety mechanism can be employed on the embodiment of FIGS. 20 and 21 allowing only one tablet at a time to be dispensed thereby avoiding the problem of a child dispensing more than one tablet. Rotation is accomplished by application of sufficient force to displace tab 99 from receiving recess 98 and advancing the dispenser housing 96 until tabs 99 align once again with recesses 98 and snap into position. At that time alignment will be achieved between a tablet holding position and opening 100.

Figure 22:
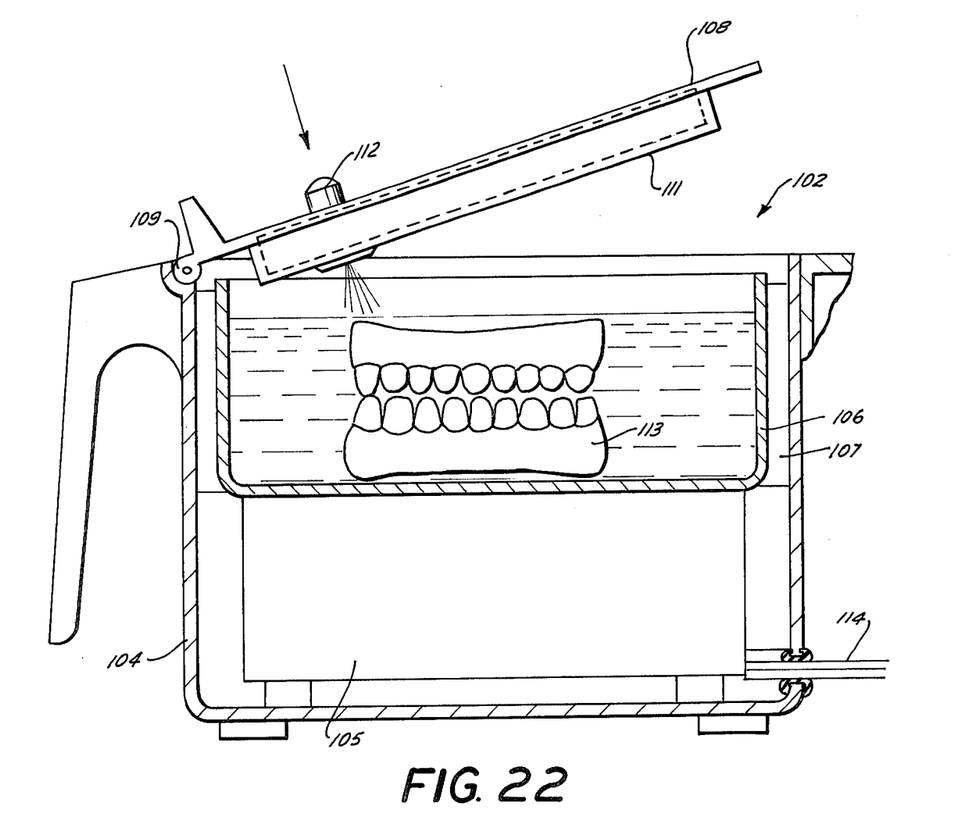
FIGS. 22 and 23 are fragmentary sectional elevation views of apparatus of the invention adapted for cleaning dentures.
Figure 23:
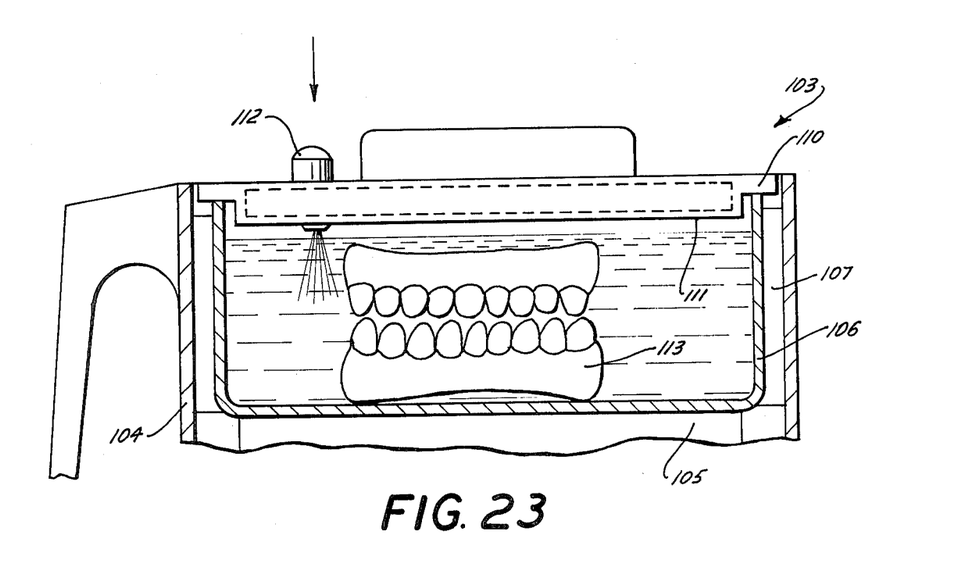

FIGS. 22 and 23 disclose the present invention as part of a denture cleaning device which can take either the form of device 102 of FIG. 22 or the form of device 103 of FIG. 23. Both examples include a similar casing 104 which contains an appropriate agitator 105 and a liquid reservoir 106 fixed to the agitator and surrounded by an elastic layer 107. In device 102, cover 108 is hinged at 109 to the casing 104. In contrast, cover 110 of device 103 is removable seated on reservoir 106. In either case the covers 108 and 110 carry a dispenser 111 attached to or integrally formed to their underside. By means of a dosage button 112 which operates the same as the previously described buttons housed in a lid, a cleaning or hygienic solution (i.e., chlorhexidine) contained in the dispenser can be introduced into the reservoir 106 that is filled with water and contains a denture 113 to be cleaned. Each device 102 and 103 is connected by a power source 114 to a suitable power supply. The agitator 105 can be preferably an ultrasonic vibrator in which case reservoir 106 must be fixed to the vibrator or a vibrator of any other conventional type. A suitable heating device may also be employed.

Figure 24:
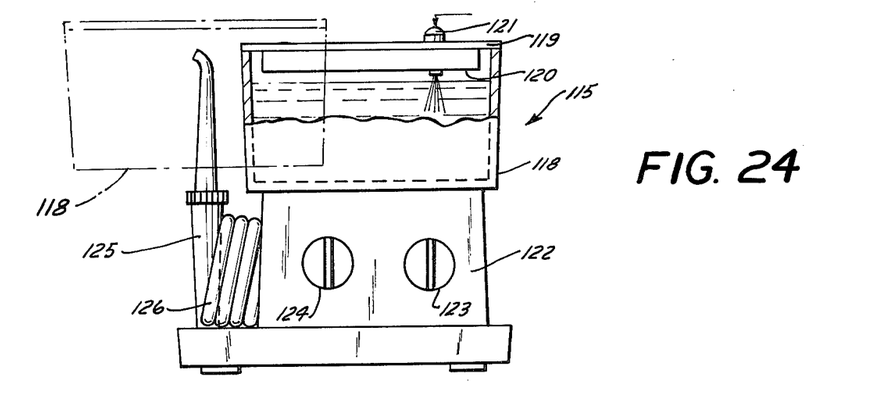
FIG. 24 is a partially sectional side elevation view of a further eleventh embodiment of the apparatus with the reservoir serving as a cover as shown in phantom.
Figure 25:
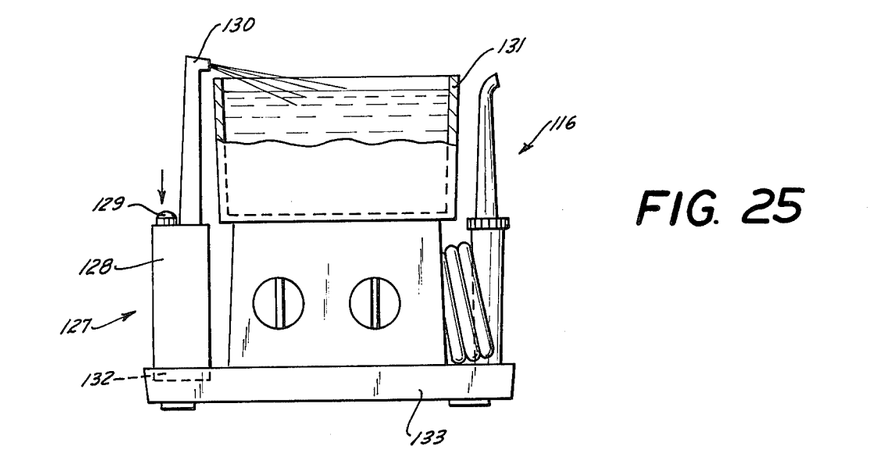
FIG. 25 is a partially sectional side elevation view of an other twelfth embodiment of the invention.
Figure 26:
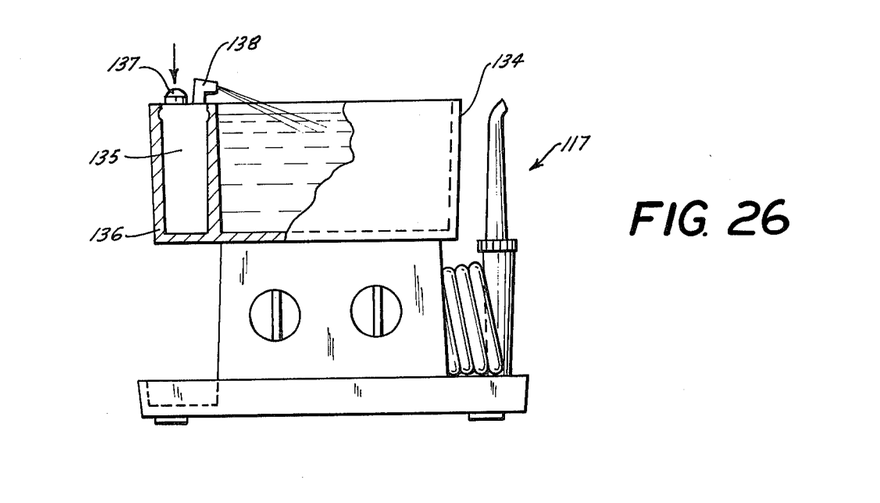
FIG. 26 is a partially sectional side elevation view of a thirteenth embodiment of the invention.

FIGS. 24, 25 and 26 disclose a series of devices 115, 116 and 117 respectively which are representative of apparatus which employ a reversible cover to act as a reservoir. In device 115, cover 118 is shown in the reversed position with the opened side up and covered by a removable lid 119 housing a dispenser 120 on its underside adapted to be operated by pushbutton 121 in a manner described with similar previous embodiments. The reservoir 18 is connected to the pump in the casing 122 in a conventional manner. Appropriate controls 123 and 124 operate the device to supply liquid to the handpiece 125 through the holes 126 in a conventional manner.

Dispenser 116 shown in FIG. 25 is identical in structure and operation to dispenser 115 with the exception of the dispenser 127. The dispenser is in the form of a cartridge 128 with a push-button 129. Fluid is dispensed from the cartridge 128 through nozzle 130 into reservoir 131. The dispenser 127 is removable seated in recess 132 in the base 133 of the casing.

The device 117 of FIG. 26 operates in a similar fashion and in this embodiment the dispenser is in the form of a cartridge 135 housed in a receptacle 136 formed integrally with cover 134. The cartridge 135 is operated by push-button 136 so that fluid from cartridge 135 is dispensed through nozzle 138 into the reservoir.

The apparatus has been described in relation to use for bucco-dental hygiene, but it is clear that similar apparatus, possibly merely with appropriate modifications in the spray head, may be used for the treatment of other parts of the body, for example the nose, ears or for local massages. In this case, the product in the dispenser for addition to the liquid in the reservoir could, as before, be a hygienic product, or alternatively be a therapeutic or cosmetic product.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

We claim:

1. Apparatus for personal hygiene, in particular for oral hygiene comprising: a casing, the casing enclosing a hydraulic pump connected by a flexible tubing to a handpiece, a reservoir removably fitted on the casing for containing a liquid supply and for supplying the liquid to the pump, a dispenser of an additive for addition to the liquid in the reservoir, the additive being a hygienic, cosmetic or therapeutic product, and means for receiving the dispenser.

2. The invention in accordance with claim 1 wherein the dispenser is removable and replaceable.

3. The invention in accordance with claim 1 wherein the receiving means for the dispenser defines a hollow recess in the upper part of the casing having a profile at least approximately adapted to the outer shape of the dispenser.

4. The apparatus in accordance with claim 3 including means defining a duct in the casing forming an outlet nozzle for the fitted dispenser.

5. Apparatus for personal hygiene, in particular for oral hygiene comprising, a casing, a reservoir fitted on the casing for containing a liquid supply, a dispenser of an additive for addition to the liquid in the reservoir, means for receiving the dispenser, the receiving means for the dispenser defining a hollow recess in the upper part of the casing having a profile at least approximately adapted to the outer shape of the dispenser, the dispenser having an outlet nozzle which, when the dispenser is in said recess, is directed into the fitted reservoir, without obstructing manipulation of the reservoir.

6. Apparatus for personal hygiene, in particular for oral hygiene comprising; a casing, a reservoir fitted on the casing for containing a liquid supply, a dispenser of an additive for addition to the liquid in the reservoir, means for receiving the dispenser, the receiving means for the dispenser defining a hollow recess in the upper part of the casing having a profile at least approximately adapted to the outer shape of the dispenser, the dispenser having an outlet nozzle which, when the dispenser is in said recess, is directed into the fitted reservoir, without obstructing manipulation of the reservoir, the reservoir having a pivoted lid which can be opened and closed without obstruction by said nozzle.

7. Apparatus for personal hygiene, in particular for oral hygiene comprising; a casing, a reservoir fitted on the casing for containing a liquid supply, a dispenser of an additive for addition to the liquid in the reservoir, means for receiving the dispenser, the receiving means for the dispenser defining a hollow recess in the upper part of the casing having a profile at least approximately adapted to the outer shape of the dispenser, the dispenser having an outlet nozzle which, when the dispenser is in said recess, is directed into the fitted reservoir, without obstructing manipulation of the reservoir, said casing having a lateral projection defining a shelf on which the reservoir rests, and said reservoir having lateral walls and a pivoted lid which when the reservoir is fitted on the casing lie in extension of corresponding faces of the casing, said recess being located in a zone of the casing adjacent the reservoir and having a depth such that the greater part of the height of the dispenser is contained in the recess.

8. The apparatus in accordance with claim 1 in which the dispenser includes dosing valve means for dispensing equal doses each time the valve is actuated.

9. Apparatus for personal hygiene, in particular for oral hygiene comprising; a casing, a reservoir fitted on the casing for containing a liquid supply, a dispenser of an additive for addition to the liquid in the reservoir, means for receiving the dispensing, the dispenser including dosage valve means for dispensing equal doses each time the valve is actuated, the dosing valve means acts by air pressure and is controlled by a push button.

10. The invention in accordance with claim 1 wherein said receiving means is incorporated in the casing.

11. The invention in accordance with claim 1 wherein said receiving means is incorporated in the reservoir.

12. Apparatus for personal hygiene, in particular for oral hygiene comprising; a casing, a reservoir fitted on the casing for containing a liquid supply, a dispenser of an additive for addition to the liquid in the reservoir, means for receiving the dispenser, said receiving means being incorporated in the reservoir, the dispenser being receiving on an inner face of a lid of the reservoir.

13. The invention in accordance with claim 12 wherein said lid has an opening through which a press-button of the dispenser is accessible.

14. Apparatus for personal hygiene, in particular for oral hygiene comprising; a casing, a reservoir fitted on the casing for containing a liquid supply, a dispenser of an additive for addition of the liquid in the reservoir, means for receiving the dispenser, said receiving means being incorporated in the reservoir, the reservoir having a handle which receives the dispenser.

15. The invention in accordance with claim 12 wherein the reservoir has a lid formed integrally with the dispenser as a removable unit.

16. The invention in accordance with claim 5 wherein a lid is coupled with the reservoir and is adapted to be shifted between an open and closed position, the dispenser is in said recess, its outlet nozzle being below the level of the lid of the reservoir, the walls of the reservoir and of the casing adjacent said recess having an opening for passage of the nozzle for the delivery of the product to the reservoir even when said lid is closed.

17. The invention in accordance with claim 16 wherein the dispenser nozzle is in the form of an integral projection adapted to extend into the opening.

18. The invention in accordance with claim 16 wherein the upper part of the dispenser substantially lies in the same plane as the upper face of the casing and the lid when closed.

19. The invention in accordance with claim 12 wherein the dispenser is removably mounted on the inner face of a lid of the reservoir.

20. Apparatus for personal hygiene, in particular for oral hygiene comprising; a casing, a reservoir fitted on the casing for containing a liquid supply, a dispenser of an additive for addition to the liquid in the reservoir, means for receiving the dispenser, safety means being on the dispenser to provide for the dispensing of only a predetermined amount of solution into the reservoir when the dispenser is in position for actuation with further manipulation of the dispenser being required for further dispenser of solution.

21. Apparatus for personal hygiene, in particular for oral hygiene comprising; a casing, a reservoir fitted on the casing for containing a liquid supply, a dispenser of an additive for addition to the liquid in the reservoir, means for receiving the dispenser, the dispenser having means thereon for dispensing the dentifrice material in the form of a tablet into the reservoir containing liquid.

22. Apparatus for personal hygiene, in particular for oral hygiene comprising; a casing, a reservoir fitted on the casing for containing a liquid supply, a dispenser of an additive for addition to the liquid in the reservoir, means for receiving the dispenser, the apparatus being for a cleaning device for dentures wherein the reservoir is positioned to contain liquid with the dentures positioned therein and the dispenser is positioned to direct a solution for cleaning or hygienic purposes into the reservoir containing the dentures.

23. The invention in accordance with claim 22 wherein an agitator is on the casing to agitate the reservoir containing the dentures, liquid and solution received from the dispenser for facilitating cleaning of the dentures.

24. Apparatus for personal hygiene, in particular for oral hygiene comprising; a casing, a reservoir fitted on the casing for containing a liquid supply, a dispenser of an additive for addition to the liquid in the reservoir, means for receiving the dispenser, the apparatus being adapted to be turned upside down and interconnected with the remainder of the apparatus to act as the reservoir removably fitted on the casing for containing a liquid supply.

25. The invention in accordance with claim 24 wherein the dispenser is mounted in a lid positioned on the opened side of the cover when it is acting as the reservoir.

26. The invention in accordance with claim 24 wherein the dispenser is on the casing in position for dispensing solution into the cover when it is positioned to act as the reservoir.

27. The invention in accordance with claim 24 wherein the dispenser is located on the cover in position to dispense a solution into the cover when it is oriented to act as the reservoir.

28. The invention in accordance with claim 1 wherein the reservoir is removably fitted on the casing.

29. A dispenser for use as part of an apparatus for personal hygiene, in particular for oral hygiene, with the apparatus including a reservoir removably fitted on a casing for containing a liquid supply comprising; means on the dispenser to retain a dentifrice solution therein and to dispense the solution therefrom upon demand, and means for positioning the dispenser with respect to the apparatus so that solution can be dispensed from the dispenser into the liquid in the reservoir of the apparatus.

30. The invention in accordance with claim 29 wherein the apparatus is for bucco-dental hygiene and includes a hydraulic pump enclosed by the casing and connected by a flexible tubing to a handpiece, the reservoir being removably fitted on the casing for supplying liquid to the pump.

31. The invention in accordance with claim 30 wherein the casing includes means for receiving the dispenser in removable replaceable position thereon with the receiving means being in the form of a hollow recess in the upper part of the casing having a profile at least approximately adapted to the outer shape of the dispenser.

32. The invention in accordance with claim 30 wherein the reservoir has a pivoted lid which can be opened and closed without obstruction by the dispenser.

33. The invention in accordance with claim 30 wherein the dispenser is adapted to be housed within the casing.

34. The invention in accordance with claim 30 wherein the dispenser is adapted to be housed in the lid of the reservoir.

35. The invention in accordance with claim 29 wherein the dispenser includes dosing valve means for dispensing equal doses each time the valve is actuated.

36. The invention in accordance with claim 35 wherein said dosing valve means acts by air pressure and is controlled by a push button.

37. The invention in accordance with claim 29 wherein the dispenser is adapted to be positioned in receiving means incorporated in the reservoir.

38. The invention in accordance with claim 29 wherein the dispenser includes safety means thereon to facilitate the dispensing of a predetermined amount of solution upon actuation of the dispensing and requiring further manipulation for dispensing of further solution thereby increasing the difficulty of dispensing more than a predetermined amount of solution.

39. The invention in accordance with claim 29 wherein the dispenser includes means thereon for dispensing a medium in a solid form into the liquid in a reservoir.

40. The invention in accordance with claim 29 wherein the dispenser is adapted to be associated with an apparatus for cleaning dentures whereby the dispenser includes means for dispensing a solution into a reservoir containing dentures to be cleaned and a liquid.

41. The invention in accordance with claim 29 wherein the dispenser is adapted for use with an apparatus for oral hygiene, in particular for oral hygiene wherein the reservoir is formed by a reversible cover on the casing in position so that when the cover is shifted to the position forming a reservoir for containing liquid the dispenser is adapted to be positioned for dispensing a solution into the reservoir.

42. The invention in accordance with claim 41 wherein the dispenser is part of a lid adapted to be positioned on the cover when it is in the inverted position to form a reservoir.

43. The invention in accordance with claim 41 wherein the dispenser is adapted to be positioned on the casing in a location whereby fluid can be dispensed into the cover when it is in the position to act as a reservoir containing liquid.

44. The invention in accordance with claim 41 wherein the dispenser is adapted to be housed in a recess on the cover in position when the cover is inverted to form a reservoir containing liquid so that a solution can be dispensed from the dispenser into the reservoir.

* * * * *